United States Patent

Effland et al.

[11] 4,375,471
[45] Mar. 1, 1983

[54] 4-ARYLOXY-1,2,3,4-TETRAHYDROISOQUINOLINES

[75] Inventors: Richard C. Effland, Bridgewater; Larry Davis, Sergeantsville; Joseph T. Klein, Bridgewater, all of N.J.

[73] Assignee: Hoechst-Roussel Pharmaceuticals Inc., Somerville, N.J.

[21] Appl. No.: 235,801

[22] Filed: Feb. 19, 1981

[51] Int. Cl.³ .................. A61K 31/47; C07D 217/24; C07D 401/06
[52] U.S. Cl. ................................. 424/258; 546/141
[58] Field of Search ......................... 546/141; 424/258

[56] References Cited

U.S. PATENT DOCUMENTS

| 3,388,130 | 6/1968 | Pesson | 546/141 |
| 3,457,266 | 7/1969 | Gibas et al. | 546/141 |
| 3,629,265 | 12/1971 | Grethe et al. | 546/141 |
| 4,059,586 | 11/1977 | Mathison et al. | 546/147 |
| 4,113,869 | 9/1978 | Gardner | 546/141 |

FOREIGN PATENT DOCUMENTS 1164192 9/1969 United Kingdom ................ 546/141

OTHER PUBLICATIONS

Patent Abstract of Japan, vol. 4, No. 2, 1/9/80, p. 122c, 69[JP-A-54-138572].

Primary Examiner—Donald G. Daus
Assistant Examiner—James H. Turnipseed
Attorney, Agent, or Firm—Jerome Rosenstock

[57] ABSTRACT

This invention relates to 4-aryloxy-1,2,3,4-tetrahydroisoquinolines of the formula

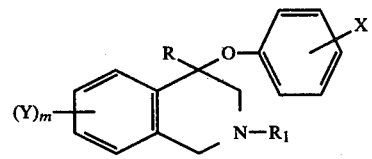

, where Y is hydrogen and alkoxy; X is hydrogen, cyano, benzoyl, trifluoromethyl, phenyl, halogen, alkyl alkoxy and nitro; R is hydrogen and alkyl; $R_1$ is hydrogen, alkyl, aralkyl,

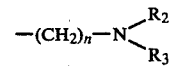

and $CO_2R_4$ where $R_4$ is aryl and alkyl; $R_2$ and $R_3$ are the same or different and are hydrogen and alkyl or $R_2$ and $R_3$ are fused together to form a pyrrolidino or a piperidino ring substituent; and m is an integer of 1 or 2; n is an integer of 2 or 3; and a pharmaceutically acceptable acid addition salt thereof.

32 Claims, No Drawings

4-ARYLOXY-1,2,3,4-TETRAHYDROISOQUINO-LINES

The compounds of the invention have the general formula

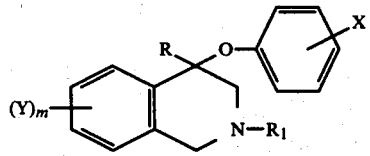

where Y is hydrogen and alkoxy; X is hydrogen, cyano, benzoyl, trifluoromethyl, phenyl, halogen, alkyl alkoxy and nitro; R is hydrogen and alkyl; $R_1$ is hydrogen, alkyl, aralkyl,

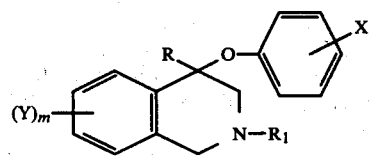

and $CO_2R_4$ where $R_4$ is aryl and alkyl; $R_2$ and $R_3$ are the same or different and are hydrogen and alkyl or $R_2$ and $R_3$ are fused together to form a pyrrolidino or a piperidino ring substituent; m is an integer of 1 or 2; n is an integer of 2 or 3; and a pharmaceutically acceptable acid addition salt thereof.

To the best of our knowledge, the compounds of the present invention have not heretofore been described or suggested.

In the above definitions and as used hereinafter, the terms "alkyl," and "alkoxy" mean the group it is describing contain 1 to 6 carbon atoms. The term "alkyl" refers to a straight or branched chain hydrocarbon containing no unsaturation. The term "alkoxy" refers to a monovalent substituent which consists of an alkyl group linked through an ether oxygen having its free valence bond from the ether oxygen. The term aralkyl refers to a straight or branched chain hydrocarbon of 1 to 6 carbon atoms containing no unsaturation in which an alkyl carbon atom is substituted by an aryl and having its free valence bond from the alkyl linkage. The term "halogen" refers to a member of the family consisting of fluorine, chlorine, bromine and iodine.

The compounds of the present invention are prepared in the following manner. The substituents Y, X, R, $R_1$, $R_2$ and $R_3$ and the members m and n are as defined earlier, unless indicated otherwise. A substituted 1,2,3,4-tetrahydro-4-isoquinolinol of the formula

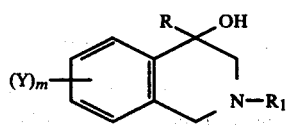

wherein R is hydrogen and $R_1$ is hydrogen, alkyl or aralkyl or a salt thereof is reacted with a substituted phenyl compound II of the formula

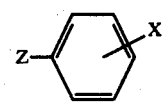

where X is as defined above and where Z is halogen, such as fluorine to form a compound of the invention

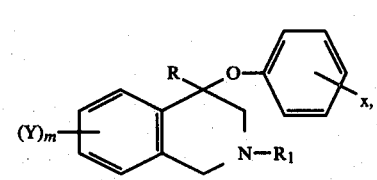

where $R_1$ is alkyl, e.g., methyl.

Compound I is generally conventionally prepared in the manner described by G. Grethe, et al, in the *Journal of Organic Chemistry*, Vol. 33, 494 (1968) which is incorporated hereinto by reference. Compound I where Y is hydrogen may be prepared in the manner described by I. G. Hinton et al, *J. Chemical Society* 599 (1959). Compound I where Y is methoxy may be prepared in the manner described by B. Umerzawa et al, *Chem. Pharm. Bull.* 19, 2138 (1971).

Typically, a salt of Compound I is first formed, in a conventional manner, as for example by reacting Compound I with sodium hydride at a temperature of 50° to 80° C. for 1 to 5 hours. The salt is then in turn reacted with Compound II, typically at a temperature of (10°–135° C.) for 5 to 20 hours to form Compound III of the invention.

Alternatively, where it is desired to have a compound of the invention where R is alkyl an isoquinoline is selected of the formula

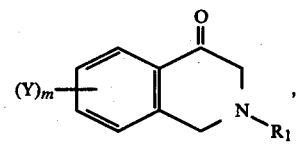

where $R_1$ is alkyl, e.g., methyl or aralkyl, e.g., benzyl. Compound IV is reacted under conventional conditions, e.g., 5° to 25° C., for 1 to 5 hours, with a Grignard reagent R -Mg Z', where R is alkyl of 1 to 6 carbon atoms, in a solvent such as ethyl ether, or THF, and Z' is a halogen, to form an alkyl substituted isoquinolinol of the formula

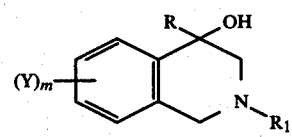

where, R is alkyl and $R_1$ is alkyl or aralkyl. Alternatively, Compound IV can be reacted with an organometallic other than the Grignard reagent to form the isoquinolinol V. Typically organometallics such as organolithium, organopotassium or organosodium compounds can be used, in a well known, conventional manner, instead of the Grignard reagent.

Compound V or a salt thereof is then reacted with Compound II, as described above, to form a Compound VI of the invention (VI)

where R is alkyl and $R_1$ is alkyl or aralkyl.

Compounds III or VI of the invention, where $R_1$ is alkyl or aralkyl are converted to their corresponding compounds of the invention where $R_1$ is $COOR_4$, where $R_4$ is alkyl of 1 to 6 carbon atoms and by reaction with a haloalkanoate having a formula $$Z''-\overset{O}{\underset{\|}{C}}-OR_4$$

where $Z''$ is halogen, to form Compound VII, an intermediate compound of the invention having the formula (VII)

where X, Y, R and $R_4$ are as originally defined. Where Compound III or VI is employed with $R_1$ being alkyl, the reaction is typically carried out at 25° to 120° C. in a solvent such as benzene or toluene in the presence of a base, such as $K_2CO_3$, $Na_2CO_3$, or $NaHCO_3$, for 1 to 20 hours. Where Compound III or VI is employed with $R_1$ being aralkyl, the reaction with the haloalkanoate, $$Z''-\overset{O}{\underset{\|}{C}}-OR_4,$$

is typically carried out at 5° to 110° C. in a solvent such as chloroform, toluene or dichloromethane, in the presence of a base, such as triethylamine, for 5 to 20 hours.

Compound VII can be hydrolyzed, in a conventional manner, under basic conditions, to form Compounds VIII of the invention where $R_1$ is hydrogen.

(VIII)

Typically, the hydrolysis is is carried out in an aqueous alcoholic solution of a base, e.g. KOH, at a temperature of 80° to 120° C. for 5 to 20 hours.

Compound VIII, is reacted with a haloalkylamine of the formula $$Z'''-(CH_2)_n-N\begin{subarray}{l}R_2\\R_3\end{subarray},\quad (IX)$$

where $Z'''$ is halogen, to form a compound of the invention having the formula (X)

Typically, the reaction is carried out in the presence of a base, e.g., $K_2CO_3$, and an iodide, e.g., KI, with a solvent, such as butanol, at a temperature of 50° to 120° C. for 5 to 20 hours.

The compounds of the invention are primarily useful as analgesic and anticonvulsant agents. The compounds of the invention are useful as analgesic agents due to their ability to alleviate pain in mammals which is demonstrated in the phenyl-para-quinone writhing assay in mice, a standard assay for analgesia [Proc. Soc. Exptl. Biol. Med., 95, 729 (1953)]. Listed below in Table III is the analgesic effect of some of the compounds of the invention, expressed as percent inhibition of phenyl-para-quinone induced writhing.

TABLE III

| Compound | Dose (Subcutaneous) (mg/kg) | % Inhibition |
|---|---|---|
| 1,2,3,4-tetrahydro-4-(p-trifluoromethylphenyl)isoquinoline hydrochloride | 25.0 | 51 |
| 2-(3-dimethylaminopropyl)-1,2,3,4-tetrahydro-4-(m-trifluoromethylphenoxy)isoquinoline dimaleate | 25.0 | 53 |
| 2-(2-N,N—dimethylaminoethyl)-1,2,3,4-tetrahydro-4-(p-trifluoromethylphenoxy)isoquinoline dihydrochloride | 14.4 | 50 |
| 2-(2-N,N—diethylaminoethyl)-1,2,3,4-tetrahydro-4-(p-trifluoromethylphenoxy)isoquinoline dioxalate | 21.8 | 50 |
| 2-(3-piperidinopropyl)-1,2,3,4-tetrahydro-4-(p-trifluoromethylphenoxy)isoquinoline dioxalate | 15.4 | 50 |
| 4-(p-nitrophenoxy)-1,2,3,4-tetrahydroisoquinoline maleate | 25.0 | 65 |
| 2-(3-N,N—dimethylaminopropyl)-4-(p-nitrophenoxy)-1,2,3,4-tetrahydroisoquinoline dihydrochloride | 14.7 | 50 |
| Propoxyphene (standard) | 3.9 | 50 |

The analgesic effect is achieved when the compounds of the invention are administered to a subject requiring such treatment at an effective oral, parenteral or intravenous dose of from 1 to 100 mg/kg of body weight per day. A preferred effective dose within this range is from about 15 to 50 mg/kg of body weight per day.

The compounds of the present invention are also useful as anticonvulsant agents for mammals as evidenced by the supra maximal electroshock assay of Woodbury, L. A. and Davenport, U. D. in Arch. Int. Pharmacodynam, Vol. 92 (1952) at pages 97–107.

In this method, groups of male mice are used (Charles River, CD-1), 18–30 grams. Drugs are prepared using distilled water and if insoluble, a surfactant is added. Control animals receive vehicle. Drugs are routinely administered intraperitoneally. The route of administration may be varied (orally, subcutaneously). The dosage volume is 10 ml/kg.

The animal's eyes are placed across the output terminals of an A.C. shocker that delivers 205 volts rms for 300 milliseconds. Electrode paste coats the animal's eyes at the point of contact with the terminals.

A compound is considered to give protection if the mouse does not exhibit extensor tonus. Protection is expressed as normalized percent inhibition relative to vehicle control.

A time response is carried out using 6 animals per group. Animals are tested at 30, 60 and 120 minutes post-drug. Additional time periods are tested if indicated by previous tests.

Listed below in Table II is the anticonvulsant effect of some of the compounds of the invention expressed as percent inhibition.

TABLE II

| Compound | Dose (Intraperitoneal) (mg/kg) | % Inhibition |
|---|---|---|
| 2-methyl-1,2,3,4-tetrahydro-4-(p-trifluoromethylphenoxy)isoquinoline oxalate | 50.0 | 50 |
| 1,2,3,4-tetrahydro-4-(p-trifluoromethylphenoxy)isoquinoline hydrochloride | 35.0 | 50 |
| 2-(3-dimethylaminopropyl)-1,2,3,4-tetrahydro-4-(p-trifluoromethylphenoxy)isoquinoline dihydrochloride | 14.4 | 50 |
| 2-methyl-1,2,3,4-tetrahydro-4-(m-trifluoromethylphenoxy)isoquinoline maleate | 50.0 | 67 |
| 4-(p-chlorophenoxy)-1,2,3,4-tetrahydroisoquinoline hydrochloride | 23.4 | 50 |
| 1,2,3,4-tetrahydro-4-(m-trifluoromethylphenoxy)isoquinoline maleate | 21.0 | 50 |
| 2-(3-dimethylaminopropyl)-1,2,3,4-tetrahydro-4-(m-trifluoromethylphenoxy)isoquinoline dimaleate | 50.0 | 100 |
| 4-(p-chlorophenoxy)-2-(3-dimethylaminopropyl)-1,2,3,4-tetrahydroisoquinoline dimaleate | 50.0 | 100 |
| 2-(2-N,N—dimethylaminoethyl-1,2,3,4-tetrahydro-4-(p-trifluoromethylphenoxy)isoquinoline dihydrochloride | 10.3 | 50 |
| 2-(2-N,N—diethylaminoethyl)-1,2,3,4-tetrahydro-4-(p-trifluoromethylphenoxy)isoquinoline dioxalate | 14.8 | 50 |
| Chlorodiazepoxide (standard) | 8.0 | 50 |
| Diazepam (standard) | 1.7 | 50 |

The anticonvulsant effect is achieved when the compounds of the invention are administered to a subject requiring such treatment at an effective oral, parenteral or intravenous dose of from 10 to 100 mg/kg of body weight per day. A preferred effective dose within this range is from about 20 to 50 mg/kg of body weight per day.

Additionally, selected compounds of the present invention exhibit some antidepressant, and diuretic properties as described below.

Selected compounds of the present invention are also useful in the treatment of depression in mammals, as demonstrated by their ability to inhibit tetrabenazine-induced depression in mice [International Journal of Neuropharmacology, 8 73 (1969)], a standard assay for useful antidepressant properties. Thus, at an intraperitoneal dose of 20 mg/kg, 2-methyl-1,2,3,4-tetrahydro-4-(m-trifluoromethylphenoxy)isoquinoline maleate and 2-methyl-4-(p-nitrophenoxy)-1,2,3,4-tetrahydroisoquinoline effect a 50% inhibition and a 30% inhibition, respectively, of the ptosis of tetrabenazine-induced depression in mice. Amitriptyline, a standard compound for antidepression, exhibits a 50% inhibition of the ptosis of tetrabenazine-induced depression in mice at an intraperitoneal dose of 2 mg/kg.

Also indicative of the usefulness of selected compounds of the present invention as antidepressant in mammals, is their demonstration of effectiveness in L-5-hydroxytryptophan (5 HTP) potentiation in rats.

Groups of six male Wistar rats (150–200 grams) are used in this test procedure. Four hours prior to testing pargyline HCl is prepared and administered by subcutaneous injection at 75 mg/kg in 1% saline and at a dosage volume of 1.25 ml/kg. Thirty minutes before testing, drugs are prepared using distilled water and, if insoluble, a suitable surfactant is added. Control groups receive vehicle. Drugs are routinely administered intraperitoneally (i.p.) at a dosage volume of 10 ml.kg.

L-5-Hydroxytryptophan is prepared at 1.0 mg/kg in distilled water and is administered i.p. in volumes proportional to 10 ml/kg. Drugs are administered in a randomized manner and 5-minute post 5-HTP treatment the animals are observed for 15 minutes.

A compound is considered to potentiate 5-HTP activity if the animals exhibit continuous forelimb clonus. Potentiation is expressed as normalized percent potentiation relative to vehicle control. When a compound is observed to potentiate 5-HTP activity, a dose range using ten animals per group is run in the same manner. An effective dose (ED) is determined by probit analysis.

Thus an intraperitoneal dose of 7.8 and 4.5 mg/kg, respectively, of 2-methyl-1,2,3,4-tetrahydro-4-(m-trifluoro methylphenoxy)isoquinoline maleate and 2-methyl-4-(p-nitrophenoxy)-1,2,3,4-tetrahydroisoquinoline represent $ED_{50}$ doses. The $ED_{50}$ of amitriptyline (standard) is 7.1.

The antidepressant effect is achieved when these compounds of the invention are administered to a subject requiring such treatment at an effective oral, parenteral or intravenous dose of from 1 to 100 mg/kg of body weight per day. A preferred effective dose within this range is from about 1 to 10 mg/kg of body weight per day.

Selected compounds of the present invention are useful as diuretics. The diuretic activity of the compounds is measured in the following manner.

Groups of female Wistar rats (150–200 grams) are used and they are food deprived 16 hours prior to testing. Drugs are prepared in 1% saline and administered in a dosage volume of 15 ml/kg orally. After dosing each animal is placed in an individual metabolic cage. Water is permitted ad libitum. Urine is collected from 0–5 hours after dosing.

Each test consists of a vehicle control, a positive control group of urea treated (1000 mg/kg) and the potential diuretic agent (50 mg/kg) treated.

The individual urine samples are analyzed for sodium and/or potassium and chloride. Sodium and potassium values are typically determined using a flame photometer. Chloride determinations are typically made by a chloride analyzer. Sodium, potassium and chloride values are expressed as the mean milliequivalents (mEq)/kg/5 hrs. Diuresis is expressed as the mean milliliters (ml)/kg/5 hrs.

The mean values obtained for sodium, potassium, chloride and diuresis are expressed in a ratio to the sodium, potassium, chloride and diuresis values obtained for the urea treated group. This ratio is called the "drug to urea ratio." A drug to urea ratio greater than or equal to one for diuresis and/or sodium is indicative of diuretic activity.

The diuretic effect of some of the compounds of the invention, expressed as the ratio of (a) the mean values obtained for diuresis (urine volume) of the compound treated group to the urea treated group and (b) the mean values obtained for sodium of the compound treated group to the urea treated group, are given in Table I.

TABLE I

| COMPOUND | Dose (oral) (mg/kg) | Diuresis Drug to Urea Ratio (Vol.) | Sodium Drug to Urea Ratio |
|---|---|---|---|
| 4-(p-cyanophenoxy)-2-methyl-1,2,3,4-tetrahydroisoquinoline | 50 | 1.1 | 1.2 |
| 2-(2-N,N—dimethylaminoethyl)-1,2,3,4-tetrahydro-4-(p-trifluoromethylphenoxy)isoquinoline | 25 | 1.1 | 1.4 |
| 2-(2-N,N—diethylaminoethyl)-1,2,3,4-tetrahydro-4-(p-trifluoromethylphenoxy)isoquinoline dioxalate | 25 | 1.4 | 1.0 |
| 2-(3-piperidinopropyl)-1,2,3,4-tetrahydro-4-(p-trifluoromethylphenoxy)isoquinoline dioxalate | 10 | 1.6 | 2.2 |
| ethacrynic acid | 64 | 2.5 | |
| tienilic acid | 64 | 1.8 | |

The diuretic effect is achieved when these compounds of the invention are administered to a subject requiring such treatment at an effective oral, parenteral or intravenous dose of from 1 to 100 mg/kg of body weight per day.

It is to be understood, however, that for any particular subject, specific dosage regimens for the above described diuretic, antidepressant, anticonvulsant and analgetic activity should be adjusted according to the individual need and the professional judgment of the person administering or supervising the administration of the compounds of the invention. It is to be further understood that the dosages set forth herein are examples only and that they do not, to any extent limit the scope or practice of the invention.

Some examples of the invention are:
4-(o-methoxyphenoxy)-2-methyl-1,2,3,4-tetrahydroisoquinoline;
4(o-cyanophenoxy)-2-methyl-1,2,3,4-tetrahydroisoquinoline;
6-methoxy-2-methyl-1,2,3,4-tetrahydro-4-(p-trifluoromethylphenoxy)isoquinoline; and
2-(3-piperidinopropyl)-1,2,3,4-tetrahydro-4-(p-trifluoromethylphenoxy)isoquinoline.

As indicated in the above-described preparation of the compounds of the invention, compounds having the structural formula

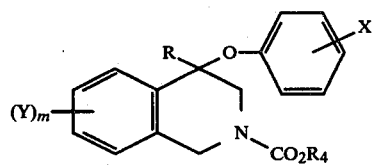

where R, X and Y are as defined above, and $R_4$ is hydrogen, lower alkyl of 1 to 6 carbon atoms and phenyl, are useful as intermediates for compounds of the invention having the structural formula

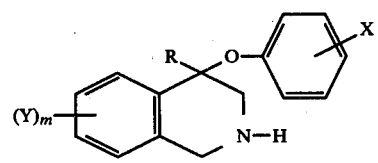

Some examples of intermediates are:
4-(p-cyanophenoxy)-2-ethoxycarbonyl-7-methoxy-1,2,3,4-tetrahydroisoquinoline;
4-(p-cyanophenoxy)-6,7-dimethoxy-2-ethoxycarbonyl-1,2,3,4-tetrahydroisoquinoline;
4-(p-benzoylphenoxy)2-ethoxycarbonyl-1,2,3,4-tetrahydroisoquinoline;
2-ethoxycarbonyl-4-(p-phenylphenoxy)-1,2,3,4-tetrahydroisoquinoline;
2-ethoxycarbonyl-4-(p-methoxyphenoxy)-1,2,3,4-tetrahydroisoquinoline; and
2-ethoxycarbonyl-4-methyl-4-(p-nitrophenoxy)-1,2,3,4-tetrahydroisoquinoline.

Effective amounts of the compounds of the present invention may be administered to a subject by one of various methods, for example, orally as in capsules or tablets, parenterally in the form of sterile solutions or suspensions, and in some cases intravenously in the form of sterile solutions. The compounds of the invention, while effective themselves, may be formulated and administered in the form of their pharmaceutically acceptable acid addition salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric, perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of at least one compound of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage unit form contains between 5.0–300 milligrams of the particular compound of the invention.

The tablets, pills, capsules, troches and the like may also contain the following adjuvants: a binder such as microcrystalline cellulose, gum tragacanth or gelatin; an excipient such as starch or lactose; a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the following adjuvants; a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes and are not to be construed as limiting the invention disclosed herein. All temperatures are given in degrees centigrade.

In view of the amendments to the Manual of Patent Examining Procedure, including Sections 608,01(p); 707.07(1); 2004; 2012 dated January, 1981 and received on or about the week of Sept. 14, 1981, Examples 1 to 32 of the specification are to be read as if they were expressed in the past tense since they are examples which have actually been carried out.

EXAMPLE 1

4-(o-Cyanophenoxy)-2-methyl-1,2,3,4-tetrahydroisoquinoline

A solution of 1,2,3,4-tetrahydro-2-methyl-4-isoquinolinol (5 g, 0.03 mole) in dimethylformamide (DMF) (15 ml) is added dropwise under nitrogen to a stirred suspension of sodium hydride 50% (98%) (1.65 g, 0.0337 mole) in freshly distilled DMF (25 ml). The mixture is warmed to 70° C. for fifteen minutes, then cooled to about 40° C. A solution of o-fluorobenzonitrile (3.71 g, 0.03 mole) in DMF (20 ml) is added dropwise and stirred at room temperature for two hours. Addition of water yields a precipitate that is filtered and washed with water to give a solid which is dried over $P_2O_5$ under vacuum to yield 6.2 g, 78.2% of product. Recrystallization from methanol affords 4-(o-cyanophenoxy)-2-methyl-1,2,3,4-tetrahydroisoquinoline, m.p. 150°–151° C., 3.8 g (48%).

ANALYSIS: Calculated for $C_{17}H_{16}N_2O$: 77.23%C; 6.11%H; 10.60%N. Found: 77.47%C; 6.20%H; 10.66%N.

EXAMPLE 2

4-(p-Cyanophenoxy)-2-methyl-1,2,3,4-tetrahydroisoquinoline

A solution of 1,2,3,4-tetrahydro-2-methyl-4-isoquinolinol (3.0 g, 0.018 mole) in dry DMF (15 ml) is added dropwise under nitrogen to a suspension of sodium hydride 50% (98%) (1.1 g, 0.022 mole), previously washed with hexane, in dry DMF (25 ml). The mixture is warmed to 60° C., at which time a solution of 4-fluorobenzonitrile (2.2 g, 0.018 mole) in dry DMF (15 ml) is slowly added. The reaction mixture is stirred at room temperature for 16 hours.

Most of the solvent is removed under reduced pressure and the resultant mixture is stirred in 500 ml water, then extracted with chloroform. The organic phase is washed twice with water, then dried (saturated NaCl, anhydrous $MgSO_4$). Removal of solvent yields a solid which is triturated with hexane then recrystallized from absolute ethanol to yield 3.3 g (68%) of a solid m.p. 131°–132° C. of 4-(p-cyanophenoxy)-2-methyl-1,2,3,4-tetrahydroisoquinoline.

ANALYSIS: Calculated for $C_{17}H_{16}N_2O$: 77.24%C; 6.10%H; 10.60%N. Found: 77.27%C; 6.10%H; 10.66%N.

EXAMPLE 3

4-(p-Benzoylphenoxy)-2-methyl-1,2,3,4-tetrahydroisoquinoline oxalate

A solution of 2-methyl-1,2,3,4-tetrahydro-4-isoquinolinol (3.0 g, 0.018 mole) in dry DMF (15 ml) is added slowly to a suspension of NaH 50% (98%) (1.1 g, 0.022 mole), previously washed with hexane, in dry DMF (25 ml). The mixture is warmed to 60° C., at which time a solution of 4-fluorobenzophenone (3.7 g, 0.018 mole) in dry DMF (15 ml) is added dropwise. The reaction mixture is allowed to stir at room temperature for 16 hours.

Most of the solvent is removed under reduced pressure and the resultant mixture is stirred in 500 ml water, then extracted with chloroform. The organic phase is washed twice with water, then dried (saturated NaCl, anhydrous $MgSO_4$). Removal of solvent yields an oil which is dissolved in ether and converted to the oxalate salt by the addition of an ethereal solution of oxalic acid. Trituration with ethyl acetate or methanol yields 3.1 g (39%) of a solid of 4-(p-benzoylphenoxy)-2-methyl-1,2,3,4-tetrahydroisoquinoline oxalate d@201° C.

ANALYSIS: Calculated for $C_{23}H_{21}NO_2 \cdot (CO_2H)_2$: 69.27%C; 5.35%H; 3.23%N. Found: 69.26%C; 5.39%H; 3.10%N.

EXAMPLE 4

4(p-Trifluoromethylphenoxy)-2-methyl-1,2,3,4-tetrahydroisoquinoline oxalate

A solution of 2-methyl-1,2,3,4-tetrahydro-4-isoquinolinol (3.0 g, 0.018 mole) in dry DMF (15 ml) is added slowly to a suspension of sodium hydride 50% (98%) (1.1 g, 0.022 mole), previously washed with hexane, in dry DMF (25 ml). After one hour p-fluorobenzotrifluoride (3.0 g, 0.018 mole) in dry DMF (15 ml) is slowly added. The reaction mixture is allowed to stir at room temperature for about 16 hours. Most of the solvent is removed under reduced pressure and the resultant mixture is stirred in 500 ml water, then extracted with chloroform. The organic phase is twice washed with water then dried (saturated NaCl, anhydrous $MgSO_4$). Removal of solvent yields an oil which is dissolved in ether and converted to the oxalate salt as in Example 3. Recrystallization from ethyl acetate-methanol (10:1) yields 4.6 g (64%) of a white solid of 4-(p-trifluoromethylphenoxy)-2-methyl-1,2,3,4-tetrahydroisoquinoline oxalate d@183° C.

ANALYSIS: Calculated for $C_{17}H_{16}F_3NO \cdot (CO_2H)_2$: 57.43%C; 4.57%H; 3.53%N. Found: 57.51%C; 4.70%H; 3.51%N.

EXAMPLE 5

4-(p-Cyanophenoxy)-2-ethoxycarbonyl-1,2,3,4-tetrahydroisoquinoline

To a solution of 2-benzyl-4-(p-cyanophenoxy)-1,2,3,4-tetrahydroisoquinoline (4.5 g; 0.013 mole) in $CHCl_3$ (50 ml) is added ethyl chloroformate (1.6 g, 0.014 mole). The mixture is allowed to reflux for two hours. The solvent is removed under reduced pressure to yield an oil which, upon trituration with ether, yields 3.1 g (73%) of a solid of 4-(p-cyanophenoxy)-2-ethoxycarbonyl-1,2,3,4-tetrahydroisoquinoline, m.p. 110° C.

ANALYSIS: Calculated for $C_{19}H_{18}N_2O_3$: 70.79%C; 5.63%H; 8.69%N. Found: 70.78%C; 5.58%H; 8.59%N.

EXAMPLE 6

4-(p-Phenylphenoxy)-2-methyl-1,2,3,4-tetrahydroisoquinoline hydrochloride

A solution of 1,2,3,4-tetrahydro-2-methyl-4-isoquinolinol (3.2 g, 0.020 mole) in 20 ml of dry DMF is added dropwise under nitrogen to a suspension of sodium hydride 50% (98%) (1.1 g, 0.022 mole), previously washed with hexane, in 15 ml dry DMF. After one hour a solution of p-fluorobiphenyl (3.4 g, 0.020 mole) in 20 ml dry DMF is added dropwise. The reaction mixture is allowed to stir at 65° C. for two hours.

Most of the solvent is removed under reduced pressure and the resultant mixture is stirred in 500 ml water, then extracted with chloroform. The organic phase is twice washed with water then dried (saturated NaCl, anhydrous $MgSO_4$). Removal of solvent yields 6 g of an oil which is purified by dry column chromatography over silica gel using ethyl acetate as the eluent. The desired product is crystallized from ether as the hydrochloride salt, yielding 1.3 g (18%) of a solid of 4-(p-phenylphenoxy-2-methyl-1,2,3,4-tetrahydroisoquinoline hydrochloride, m.p. 134° C.

ANALYSIS: Calculated for $C_{22}H_{21}NO \cdot HCl$: 75.09%C; 6.30%H; 3.98%N. Found: 75.11%C; 6.34%H; 3.92%N.

EXAMPLE 7

4-(p-Chlorophenoxy)-2-methyl-1,2,3,4-tetrahydroisoquinoline hydrochloride

A solution of 1,2,3,4-tetrahydro-2-methyl-4-isoquinolinol (3.3 g, 0.020 mole) in dry DMF is added dropwise under nitrogen to a suspension of sodium hydride 50% (98%) (1.6 g, 0.033 mole), previously washed with hexane, in 40 ml dry DMF, at 65° C. After the evolution of gas ceases, a solution of p-chlorofluorobenzene (3.6 g, 0.028 mole) in 15 ml dry DMF is added slowly, and the resulting mixture is allowed to stir at 75° C. for 16 hours. After cooling to room temperature the solution is poured into water (110 ml), extracted with chloroform, the chloroform phase is washed twice with water, dried (saturated NaCl, anhydrous $MgSO_4$) and removed via reduced pressure to yield an oil which is purified by dry column chromatography, over silica gel using ethyl acetate as the eluent. The desired product is crystallized from ether as the hydrochloride salt, yielding 1.9 g (31%) of a solid of 4-(p-chlorophenoxy)-2-methyl-1,2,3,4-tetrahydroisoquinoline hydrochloride, d@92° C.

ANALYSIS: Calculated for $C_{16}H_{16}ClNO \cdot HCl$: 61.94%C; 5.52%H; 4.52%N. Found: 61.74%C; 5.45%H; 4.56%N.

EXAMPLE 8

2-Methyl-4-phenoxy-1,2,3,4-tetrahydroisoquinoline

A solution of 2-methyl-1,2,3,4-tetrahydro-4-isoquinolinol (6.0 g, 0.037 mole) in 30 ml dry DMF is added dropwise under nitrogen to a suspension of sodium hydride 50% (98%) (2.2 g, 0.044 mole), previously washed with hexane, in 50 ml dry DMF. After one hour the mixture is slowly warmed to 75° C. at which time fluorobenzene (7.1 g. 0.074 mole) in 30 ml dry DMF is added dropwise. The reaction mixture is stirred at 95° C. for four hours then at 75° C. for about 16 hours. Most of the solvent is removed under reduced pressure and the resultant mixture is stirred in 500 ml water then extracted with chloroform. The combined organic extracts are washed twice with water then dried (saturated NaCl, anhydrous $MgSO_4$). Removal of solvent yields 5.8 g (65%) of an oil which is purified by dry column chromatography over silica gel using ethyl acetate as the eluent. The desired product is extracted with chloroform to yield 1.5 g (17%) of an oil of 2-methyl-4-phenoxy-1,2,3,4-tetrahydroisoquinoline.

ANALYSIS: Calculated for $C_{16}H_{17}NO$: 80.30%C; 7.16%H; 5.85%N. Found: 80.07%C; 7.22%H; 5.79%N.

EXAMPLE 9

6,7-Dimethoxy-2-methyl-1,2,3,4-tetrahydro-4-(p-trifluoromethylphenoxy)isoquinoline hydrochloride To a suspension of NaH (50% in oil, 1.1 g, 0.023 mole) in 10 ml DMF, is added a solution of 6,7-dimethoxy-2-methyl-1,2,3,4-tetrahydro-4-isoquinolinol (4.2 g, 0.019 mole) in 25 ml DMF. The mixture becomes warm with gas evolution, and is stirred for one hour at ambient temperature. To this is added a solution of p-(trifluoromethyl)fluorobenzene (3.1 g, 0.019 mole) in 20 ml DMF, and the mixture is stirred at ambient temperature for twenty-four hours.

The mixture is evaporated to a semi-solid, which is stirred with 500 ml water for thirty minutes, then extracted with chloroform. The chloroform layer is washed twice with water, then dried (saturated NaCl, anhydrous MgSO$_4$). After filtering, the solvent is evaporated to an oil which is dissolved in ether, then converted to a hydrochloride salt by the addition of ethereal hydrogen chloride to yield 5.8 g (76%), d@95° C. This material is recrystallized twice with ethyl acetate/methanol (10:1) to yield 3.8 g of 6,7-dimethoxy-2-methyl-1,2,3,4-tetrahydro-4-(p-trifluoromethylphenoxy)isoquinoline hydrochloride, d@145° C.

ANALYSIS: Calculated for C$_{19}$H$_{20}$F$_3$NO$_3$.HCl: 56.51%C; 5.24%H; 3.47%N. Found: 56.55%C; 5.58%H; 3.58%N.

EXAMPLE 10

4-(o-Cyanophenoxy)-6,7-dimethoxy-2-methyl-1,2,3,4-tetrahydroisoquinoline

A solution of 6,7-dimethoxy-2-methyl-1,2,3,4-tetrahydro-4-isoquinolinol (8.5 g, 0.038 mole) in dry DMF (40 ml) is added dropwise under nitrogen to a suspension of sodium hydride 50% (98%) (2.3 g, 0.046 mole), previously washed with hexane, in dry DMF (30 ml). The mixture is stirred at room temperature for one hour at which time a solution of o-fluorobenzonitrile (4.6 g, 0.038 mole) in dry DMF (30 ml) is slowly added. The reaction mixture is stirred at room temperature for about sixteen hours. The solvent is removed under reduced pressure and the resultant mixture is stirred in 500 ml water, then extracted with chloroform. The combined organic phases are washed twice with water then dried (saturated NaCl, anhydrous MgSO$_4$). Removal of solvent yields a solid (14.4 g, m.p. 120°–129° C.) which is twice recrystallized from methanol to yield 8.4 g (68%) of 4-(o-cyanophenoxy)-6,7-dimethoxy-2-methyl-1,2,3,4-tetrahydroisoquinoline, m.p. 147°–148° C.

ANALYSIS: Calculated for C$_{19}$H$_{20}$N$_2$O$_3$: 70.35%C; 6.22%H; 8.64%N. Found: 70.14%C; 6.12%H; 8.54%N.

EXAMPLE 11

2-Ethoxycarbonyl-1,2,3,4-tetrahydro-4-(p-trifluoromethylphenoxy)isoquinoline

To a solution of 2-methyl-1,2,3,4-tetrahydro-4-(p-trifluoromethylphenoxy)isoquinoline of Example 4 (18.0 g, 0.06 mole) in 200 ml benzene, is added K$_2$CO$_3$ (20 g, 0.145 mole), and, with stirring, a solution of ethyl chloroformate (7.6 g, 0.07 mole) in 50 ml benzene. After refluxing for four hours, the mixture is cooled, washed twice with 100 ml portions of water, thrice with dilute HCl solution (100 ml), twice with water (100 ml), then dried (saturated NaCl, anhydrous MgSO$_4$). After filtering, the solvent is evaporated to an oil, which solidifies upon cooling, to a solid, 13.7 g (64%), m.p. 84° C. This material is recrystallized from hexanes twice, to yield 11.0 g, m.p. 107°–109° C. of 2-ethoxycarbonyl-1,2,3,4-tetrahydro-4-(p-trifluoromethylphenoxy)isoquinoline.

ANALYSIS: Calculated for C$_{19}$H$_{18}$F$_3$NO$_3$: 62.46%C; 4.97%H; 3.83%N. Found: 62.59%C; 5.10%H; 3.84%N.

EXAMPLE 12

2-Methyl-1,2,3,4-tetrahydro-4-(m-trifluoromethylphenoxy)isoquinoline maleate

To a suspension of NaH (50% in oil, 7.2 g, 0.15 mole) in 25 ml DMF, is added a solution of 2-methyl-1,2,3,4-tetrahydro-4-isoquinolinol (20.0 g, 0.123 mole) in 50 ml DMF in about thirty minutes. The mixture becomes warm with a vigorous evolution of gas. After stirring at ambient temperature for one hour, a solution of m-trifluoromethylfluorobenzene (24.6 g, 0.15 mole) in 50 ml DMF is added in about thirty minutes. After stirring at ambient temperature for twenty hours the reaction mixture is concentrated to an oil which is poured into 500 ml water, and stirred for 30 minutes. The resultant solution is extracted with chloroform and the chloroform extract washed twice with water, then dried (saturated NaCl, anhydrous MgSO$_4$). After filtering, the solvent is evaporated to an oil, which is dissolved in ether, and the HCl-salt precipitated by the addition of ethereal hydrogen chloride. The salt is washed with ether, dissolved in water, neutralized with saturated Na$_2$CO$_3$ solution, then extracted with ether. The ether layer is washed twice with water then dried (saturated NaCl, anhydrous MgSO$_4$).

After filtering, the solvent is evaporated to an oil, which upon standing in the cold solidifies to a solid, 26 g (69%) m.p. 50° C. A sample of this solid is converted to a maleate salt by the addition of ethereal maleic acid, and recrystallization twice from ethyl acetate/ether (5:1) yields 4.0 g of 2-methyl-1,2,3,4-tetrahydro-4-(m-trifluoromethylphenoxy)isoquinoline maleate, m.p. 121°–123° C.

ANALYSIS: Calculated for C$_{17}$H$_{16}$F$_3$NO.C$_4$H$_4$O$_4$: 59.57%C; 4.76%H; 3.31%N. Found: 59.73%C; 4.86%H; 3.41%N.

EXAMPLE 13

2-Ethoxycarbonyl-1,2,3,4-tetrahydro-4-(m-trifluoromethylphenoxy)isoquinoline

To 250 ml benzene, is added 2-methyl-1,2,3,4-tetrahydro-4-(m-trifluoromethylphenoxy)isoquinoline (22.0 g, 0.072 mole) of Example 12, K$_2$CO$_3$ (20.0 g, 0.145 mole), and ethyl chloroformate (10.8 g, 0.1 mole).

After stirring at reflux for twenty-four hours, the mixture is cooled, washed twice with water, thrice with dilute HCl solution, twice with water, then dried (saturated NaCl, anhydrous MgSO$_4$). After filtering the solvent is evaporated to an oil, which solidified to a solid upon trituration with petroleum ether, to yield 18 g (70%) m.p. 94°–96° C. A sample of this material is recrystallized twice from hexanes, to yield a solid of 2-ethoxycarbonyl-1,2,3,4-tetrahydro-4-(m-trifluoromethylphenoxy)isoquinoline, m.p. 98°–100° C.

ANALYSIS: Calculated for C$_{19}$H$_{18}$F$_3$NO$_3$: 62.46%C; 4.97%H; 3.83%N. Found: 62.61%C; 4.95%H; 3.87%N.

EXAMPLE 14

1,2,3,4-Tetrahydro-4-(p-trifluoromethylphenoxy)isoquinoline hydrochloride

A mixture of 2-ethoxycarbonyl-1,2,3,4-tetrahydro-4-(p-trifluoromethylphenoxy)isoquinoline (21.7 g, 0.059 mole) of Example 13, KOH (25 g, 0.05 mole) and water (25 ml) in 300 ml n-propanol is refluxed for 4.5 hours. After cooling, the solvent is removed to yield an oil which is stirred in 500 ml water, then extracted with chloroform. The combined organic phases are washed twice with water, then dried (saturated NaCl, anhydrous MgSO$_4$). Removal of solvent yields 15.4 g (89%) of a solid, of which 1.0 g is dissolved in ether and converted to the hydrochloride salt (1.0 g, d@174°–187° C.) by the addition of ethereal hydrogen chloride. This material is twice recrystallized from ethyl acetate to yield 0.8 g (73%) of 1,2,3,4-tetrahydro-4-(p-trifluoromethylphenoxy)isoquinoline hydrochloride, d@202° C.

ANALYSIS: Calculated for $C_{16}H_{14}F_3NO·HCl$: 58.28%C; 4.59%H; 4.25%N. Found: 58.13%C; 4.88%H; 4.06%N.

EXAMPLE 15

2-(3-Dimethylaminopropyl)-1,2,3,4-tetrahydro-4-(p-trifluoromethylphenoxy)isoquinoline dihydrochloride A mixture of 1,2,3,4-tetrahydro-4-(p-trifluoromethylphenoxy)isoquinoline of Example 14 (4.9 g, 0.017 mole), 3-dimethylaminopropyl chloride (2.5 g, 0.021 mole), potassium carbonate (20 g) and KI (0.01 g) in 100 ml n-butanol is refluxed for seven hours.

The reaction mixture is filtered and the solvent is removed to yield an oil which is stirred in 500 ml water then extracted with ether. The combined ether extracts are washed twice with water then dried (saturated NaCl, anhydrous $MgSO_4$). After filtering, the solvent is removed to yield an oil which is dissolved in ether, then converted to the dihydrochloride salt (5.8 g, 92%) by the addition of ethereal hydrogen chloride.

This material is twice recrystallized from ethyl acetate-methanol (10:1) to yield 2.6 g (34%) of 2-(3-dimethylaminopropyl)-1,2,3,4-tetrahydro-4-(p-trifluoromethylphenoxy)isoquinoline dihydrochloride.

ANALYSIS: Calculated for $C_{21}H_{25}F_3N_2O·2HCl$: 55.88%C; 6.03%H; 6.21%N. Found: 55.70%C; 6.13%H; 5.97%N.

EXAMPLE 16

4-(p-Chlorophenoxy)-2-ethoxycarbonyl-1,2,3,4-tetrahydroisoquinoline

A mixture of 4-(p-chlorophenoxy)-2-methyl-1,2,3,4-tetrahydroisoquinoline of Example 7, (22.1 g, 0.08 mole), ethyl chloroformate (10.9 g, 0.1 mole) and $K_2CO_3$ (22 g) in benzene (250 ml) is refluxed seven hours.

The reaction mixture is filtered, diluted with ether (400 ml), washed with water, dilute HCl, again with water, then dried (saturated NaCl, anhydrous $MgSO_4$). After filtering, the solvent is removed to yield 21.5 g of an oil, which upon trituration with petroleum ether yields 14.6 g (63% based on recovered starting material) of a solid, m.p. 62°–68° C. An analytical sample is twice recrystallized from hexanes to yield 4-(p-chlorophenoxy)-2-ethoxycarbonyl-1,2,3,4-tetrahydroisoquinoline, m.p. 78.5°–79.5° C.

ANALYSIS: Calculated for $C_{18}H_{18}ClNO_3$: 65.16%C; 5.47%H; 4.22%N. Found: 65.20%C; 5.48%H; 4.12%N.

EXAMPLE 17

4-(p-Chlorophenoxy)-1,2,3,4-tetrahydroisoquinoline hydrochloride

A mixture of 4-(p-chlorophenoxy-2-ethoxycarbonyl-1,2,3,4-tetrahydroisoquinoline of Example 16 (13.0 g, 0.04 mole), KOH (14 g) and water (14 ml) in n-propanol (170 ml) is refluxed for four hours. Removal of solvent under reduced pressure yields an oil which is stirred in water (500 ml) then extracted with ether. The combined organic extracts are washed with water, then dried (saturated NaCl, anhydrous $MgSO_4$). After filtering, the solvent is removed to yield 9.4 g (90%) of an oil of which 4.0 g is dissolved in ether and converted to the hydrochloride salt (3.8 g, 83%, d@184°–188° C.) by the addition of ethereal hydrogen chloride. An analytical sample is twice recrystallized from ethyl acetate/methanol (10:1) to yield 4-(p-chlorophenoxy)-1,2,3,4-tetrahydroisoquinoline hydrochloride, d@199° C.

ANALYSIS: Calculated for $C_{15}H_{14}ClNO·HCl$: 60.82%C; 5.10%H; 4.73%N. Found: 60.96%C; 5.17%H; 4.72%N.

EXAMPLE 18

1,2,3,4-Tetrahydro-4-(m-trifluoromethylphenoxy)isoquinoline maleate

To a solution of potassium hydroxide (14.0 g, 0.25 mole) in 14 ml water, is added a solution of 2-ethoxycarbonyl-1,2,3,4-tetrahydro-4-(m-trifluoromethylphenoxy)isoquinoline of Example 13 (11.5 g, 0.0315 mole) in 170 ml n-propanol, and the mixture is stirred at reflux for four hours. After cooling, the solvent is evaporated to a semi-solid, which is stirred with 500 ml water for fifteen minutes, then extracted with ether. The ether extract is washed twice with water, then dried (saturated NaCl, anhydrous $MgSO_4$).

After filtering twice, the solvent is evaporated to an oil, which is converted to a maleate salt by the addition of an ethereal solution of maleic acid to yield 10.8 g (84%), m.p. 127°–129° C. A sample of this is recrystallized twice from ethyl acetate/ether, (1:1) to yield 1,2,3,4-tetrahydro-4-(m-trifluoromethylphenoxy)isoquinoline maleate, m.p. 128°–129° C.

ANALYSIS: Calculated for $C_{16}H_{14}F_3NO·C_4H_4O_4$: 58.68%C; 4.43%H; 3.42%N. Found: 58.71%C; 4.46%H; 3.40%N.

EXAMPLE 19

2-(3-Dimethylaminopropyl)-1,2,3,4-tetrahydro-4-(m-trifluoromethylphenoxy)isoquinoline dimaleate To 100 ml n-butanol is added 1,2,3,4-tetrahydro-4-(m-trifluoromethylphenoxy)isoquinoline of Example 18 (4.4 g, 0.016 mole), dimethylaminopropyl chloride (3.0 g, 0.027 mole), $K_2CO_3$ (20.0 g, 0.145 mole), and 0.01 g of KI.

After stirring at reflux for twenty hours, the mixture is cooled, and the solvent evaporated to an oil, which is stirred with 500 ml water for fifteen minutes, then extracted with ether. The ether extract is washed twice with water, then dried (saturated NaCl, anhydrous $MgSO_4$). After filtering, the solvent is evaporated to an oil which is converted to a dimaleate salt by the addition of an ethereal solution of maleic acid to yield 5.2 g (57%), m.p. 90° C. This material is recrystallized twice from ethyl acetate/methanol (10:1) to yield 3.0 g of 2-(3-dimethylaminopropyl)-1,2,3,4-tetrahydro-4-(m-trifluoromethylphenoxy)isoquinoline dimaleate, m.p. 168°–170° C.

ANALYSIS: Calculated for $C_{21}H_{25}F_3N_2O·2C_4H_4O_4$: 57.04%C; 5.45%H; 4.59%N. Found: 57.05%C; 5.28%H; 4.52%N.

EXAMPLE 20

4-(p-Chlorophenoxy)-2-(3-dimethylaminopropyl)-1,2,3,4-tetrahydroisoquinoline dimaleate To 100 ml n-butanol is added 4-(p-chlorophenoxy)-1,2,3,4-tetrahydroisoquinoline of Example 7 (5.2 g, 0.02 mole), dimethylaminopropyl chloride (5.0 g, 0.04 mole), $K_2CO_3$ (20.0 g, 0.145 mole), and 0.01 g of KI.

After stirring at reflux (120° C.) for twenty hours, the mixture is cooled, filtered, and the filtrate evaporated to an oil, which is stirred with 500 ml water for fifteen minutes, then extracted with ether. The ether extract is washed thrice with water, then dried (saturated NaCl, anhydrous MgSO₄). After filtering, the solvent is evaporated to an oil, which is converted to a dimaleate salt by the addition of an ethereal solution of maleic acid to yield 4-(p-chlorophenoxy)-2-(3-dimethylaminopropyl)-1,2,3,4-tetrahydroisoquinoline dimaleate, 5.0 g, m.p. 169°–171° C.

ANALYSIS: Calculated for $C_{20}H_{25}ClN_2O.2C_4H_4O_4$: 58.28%C; 5.76%H; 4.86%N. Found: 58.29%C; 5.91%H; 4.80%N.

EXAMPLE 21

A. 2,4-Dimethyl-1,2,3,4-tetrahydroisoquinoline-4-ol hydrochloride

To a solution of methyl magnesium chloride (13.9 g, 0.19 mole) in THF (68 ml), cooled to 10° C., is added slowly 2-methyl-2,3-dihydro-4(1H)-isoquinolone (20.0 g, 0.12 mole) in THF (80 ml). After the addition is completed the reaction mixture is allowed to warm to room temperature. The reaction mixture is poured slowly into one liter saturated NH₄Cl and stirred, then extracted with ether. The combined ethereal extracts are washed twice with water then dried (saturated NaCl, anhydrous MgSO₄). After filtering, removal of solvent yields 20.5 g (93%) of a liquid which solidifies on cooling. 4.0 g of this material is dissolved in ether and is then converted to the hydrochloride salt by the addition of ethereal hydrogen chloride to yield 4.7 g, 98%, m.p. 183°–187° C. An analytical sample is obtained by twice recrystallizing a 1.0 g sample to yield a solid of 2,4-dimethyl-1,2,3,4-tetrahydroisoquinoline-4-ol hydrochloride, d@189°–190° C.

ANALYSIS: Calculated for $C_{11}H_{15}NO.HCl$: 61.82%C; 7.55%H; 6.56%N. Found: 61.92%C; 7.48%H; 6.50%N.

B. 2,4-Dimethyl-1,2,3,4-tetrahydro-4-(p-trifluoromethylphenoxy)isoquinoline

A solution of 2,4-dimethyl-1,2,3,4-tetrahydroisoquinolin-4-ol (16.6 g, 0.093 mole) of Example 21A in dry DMF (50 ml) is added dropwise under nitrogen to a stirred suspension of sodium hydride 50% (98%) (5.5 g, 0.11 mole), previously washed with hexane, in dry DMF (50 ml). After the addition is completed the mixture is stirred at room temperature for one hour then is warmed to 70° C. for one hour, at which time p-fluorobenzotrifluoride (16.8 g, 0.10 mole) in DMF (30 ml) is added slowly. The reaction mixture is then warmed to 100° C. for nine hours. Most of the solvent is removed under reduced pressure and the resultant mixture is stirred in water (500 ml), then extracted with chloroform. The combined organic extracts are washed twice with water then dried (saturated NaCl, anhydrous MgSO₄). Removal of solvent yields 15.6 g (52%) of an oil which is purified by dry column chromatography over silica gel using ethyl acetate as the eluent. The desired product is extracted with chloroform to yield 7.7 g (26%) of an oil of which 3.4 g is dissolved in ether and is then converted to the hydrochloride salt by the addition of ethereal hydrogen chloride to yield (3.7 g, 98%, m.p. 125°–136° C.). An analytical sample is twice recrystallized from ethyl acetate to yield 2,4-dimethyl-1,2,3,4-tetrahydro-4-(p-trifluoromethylphenoxy)isoquinoline hydrochloride, m.p. 145°–45.5° C.

ANALYSIS: Calculated for $C_{18}H_{18}F_3NO.HCl$: 60.42%C; 5.35%H; 3.92%N; Found: 60.17%C; 5.43%H; 3.93%N.

EXAMPLE 22

4-(o-Methoxyphenoxy)-2-methyl-1,2,3,4-tetrahydroisoquinoline hydrochloride

A solution of 2-methyl-1,2,3,4-tetrahydro-4-isoquinolinol (11.4 g, 0.070 mole) in 40 ml DMF is added dropwise under nitrogen to a suspension of NaH 50% (98%) (4.1 g 0.084 mole), previously washed with hexane, in 20 ml DMF. After one hour 2-fluoroanisole (11.5 g, 0.091 mole) in 40 ml DMF is added dropwise. The reaction mixture is stirred at 130°–135° for eight hours. Most of the solvent is removed under reduced pressure and the resultant oil is stirred in 500 ml water, then extracted with ether. The combined organic extracts are washed twice with water then dried (saturated NaCl, anhydrous MgSO₄). Removal of solvent yields 12.4 g of an oil which is purified by dry column chromatography over silica gel using ethyl acetate as the eluent. The desired product is extracted with chloroform to yield 2.7 g (14%) of a solid which is dissolved in ether, then converted to the hydrochloride salt of 4-(o-methoxyphenoxy)-2-methyl-1,2,3,4-tetrahydroisoquinoline hydrochloride by the addition of ethereal hydrogen chloride (2.2 g, m.p. 79°–81° C.).

ANALYSIS: Calculated for $C_{17}H_{19}NO_2.HCl$: 66.77%C; 6.59%H; 4.58%N. Found: 66.26%C; 6.59%H; 4.65%N.

EXAMPLE 23

2-Methyl-4-(p-nitrophenoxy)-1,2,3,4-tetrahydroisoquinoline

A solution of 2-methyl-1,2,3,4-tetrahydro-4-isoquinolinol (5.0 g, 0.031 mole) in dry DMF (30 ml) is added dropwise under nitrogen to a stirred suspension of sodium hydride 50% (98%) (1.8 g, 0.037 mole), previously washed with hexane, in dry DMF (10 ml). After the addition is completed the mixture is warmed to 60° C. for one hour, then cooled to 0°–5° C. with an ice bath. A solution of 1-fluoro-4-nitrobenzene (5.6 g, 0.040 mole) in DMF (20 ml) is then slowly added at a rate such that the reaction mixture temperature does not exceed 10° C. After the addition is completed the reaction mixture is allowed to warm to room temperature for two hours.

The solvent is removed under reduced pressure and the resultant mixture is stirred in water (400 ml), then extracted with chloroform. The combined organic phases are washed with water, then dried (saturated NaCl, anhydrous MgSO₄). After filtering, the solvent is removed to yield a solid which is triturated with hexane to yield 8.5 g (97%), m.p. 125°–133° C. An analytical sample is twice recrystallized from absolute ethanol to yield 2-methyl-4-(p-nitrophenoxy)-1,2,3,4-tetrahydroisoquinoline, m.p. 141.5°–143° C.

ANALYSIS: Calculated for $C_{16}H_{16}N_2O_3$: 67.59%C; 5.67%H; 9.86%N. Found: 67.40%C; 5.55%H; 9.93%N.

EXAMPLE 24

2-Ethoxycarbonyl-4-(p-nitrophenoxy)-1,2,3,4-tetrahydroisoquinoline

A mixture of 2-methyl-4-(p-nitrophenoxy)-1,2,3,4-tetrahydroisoquinoline of Example 23 (6.0 g, 0.021 mole), ethyl chloroformate (2.9 g, 0.026 mole) and potassium carbonate (10 g) in benzene (100 ml) is refluxed for four hours. The reaction mixture is diluted with ether, washed with water, dilute HCl, again with water, then dried (saturated NaCl, anhydrous MgSO4). An analytical sample is twice recrystallized from hexanes/acetone (10:1) to yield 2-ethoxycarbonyl-4-(p-nitrophenoxy)-1,2,3,4-tetrahydroisoquinoline, m.p. 118°–119° C.

ANALYSIS: Calculated for $C_{18}H_{18}N_2O_5$: 63.15%C; 5.30%H; 8.18%N; Found: 63.37%C; 5.31%H; 8.25%N.

EXAMPLE 25

2,4-Dimethyl-4-(p-nitrophenoxy)-1,2,3,4-tetrahydroisoquinoline hydrochloride

A solution of 2,4-dimethyl-1,2,3,4-tetrahydro-4-isoquinolinol (10.0 g, 0.056 mole) in dry DMF (50 ml) is added dropwise under nitrogen to a stirred suspension of sodium hydride 50% (98%) (3.3 g, 0.068 mole), previously washed with hexane, in dry DMF (20 ml). After the addition is completed the mixture is warmed at 65° C. for two hours to insure salt formation, then cooled to 5° C. with an ice bath. A solution of 1-fluoro-4-nitrobenzene (9.2 g, 0.065 mole) in DMF (20 ml) is then slowly added dropwise. The reaction mixture is warmed at 70° C. for four hours. The solvent is removed under reduced pressure and the resultant mixture is stirred with water, then extracted with chloroform. The combined organic phases are washed twice with water, then dried (saturated NaCl, anhydrous MgSO4). The solution filtered, then concentrated to an oil which is dissolved in ether, then converted to the hydrochloride salt by the addition of ethereal hydrogen chloride to yield (18.6 g, 94%, m.p. 82°–90° C.). A 5.5 g sample is twice recrystallized from ethyl acetate/methanol (5:1) to yield 2,4-dimethyl-4-(p-nitrophenoxy)-1,2,3,4-tetrahydroisoquinoline hydrochloride (2.7 g, m.p. 131°–132° C.).

ANALYSIS: Calculated for $C_{17}H_{18}N_2O_3 \cdot HCl$: 60.98%C; 5.72%H; 8.37%N. Found: 61.23%C; 5.88%H; 8.49%N.

EXAMPLE 26

2-Phenoxycarbonyl-1,2,3,4-tetrahydro-4-(p-trifluoromethylphenoxy)isoquinoline

To a cold solution of 2-methyl-1,2,3,4-tetrahydro-4-(p-trifluoromethylphenoxy)isoquinoline of Example 4 (23 g, 0.075 mole) in 150 ml dichloromethane, is added 25 g $K_2CO_3$, followed by a solution of phenyl chloroformate (15.6 g, 0.1 mole) in 100 ml dichloromethane. After stirring at ambient temperature for twenty hours, the mixture is filtered, and the solvent evaporated to an oil, which solidifies to a solid upon trituration with hexanes, 24 g (80%), m.p. 72° C. A sample of this material is recrystallized twice from hexanes, to yield 2-phenoxycarbonyl-1,2,3,4-tetrahydro-4-(p-trifluoromethylphenoxy)isoquinoline, m.p. 101°–3° C.

ANALYSIS: Calculated for $C_{23}H_{18}F_3NO_3$: 66.82%C; 4.39%H; 3.39%N. Found: 67.18%C; 4.47%H; 3.30%N.

EXAMPLE 27

2-(2-N,N-Dimethylaminoethyl)-4-(p-trifluoromethylphenoxy)-1,2,3,4-tetrahydroisoquinoline dihydrochloride A mixture of 1,2,3,4-tetrahydro-4-(p-trifluoromethylphenoxy)isoquinoline of Example 8 (5.0 g, 0.017 mole), 2-dimethylaminoethyl chloride (3.7 g, 0.034 mole), $K_2CO_3$ (10 g) and 0.01 g. of KI in n-butanol (100 ml) is refluxed for two hours.

The mixture is cooled, filtered, then concentrated to an oil which is stirred with water then extracted with ether. The combined ether extracts are washed twice with water then dried (saturated NaCl, anhydrous MgSO4).

The solution is filtered then concentrated to an oil (4.0 g) which is dissolved in ether and then converted to the dihydrochloride salt (3.6 g gummy solid, 49%) by the addition of ethereal hydrogen chloride. This material is twice recrystallized from ethyl acetate/methanol (10:1) to yield 2-(2-N,N-dimethylaminoethyl)-4-(p-trifluoromethylphenoxy)-1,2,3,4-tetrahydroisoquinoline dihydrochloride (1.7 g, d@194°–195° C.).

ANALYSIS: Calculated for $C_{20}H_{23}F_3N_2O \cdot 2HCl$: 54.92%C; 5.76%H; 6.41%N. Found: 54.99%C; 5.95%H; 6.32%N.

EXAMPLE 28

2-(2-N,N-Diethylaminoethyl)-4-(p-trifluoromethylphenoxy)-1,2,3,4-tetrahydroisoquinoline dioxalate A mixture of 1,2,3,4-tetrahydro-4-(p-trifluoromethylphenoxy)isoquinoline of Example 8 (5.0 g, 0.017 mole), 2-diethylaminoethyl chloride (4.6 g, 0.034 mole), $K_2CO_3$ (10 g) and 0.01 g. KI in n-butanol (100 ml) is refluxed for 2.5 hours.

Removal of solvent yields an oil which is stirred with water then extracted with ether. The combined ether extracts are washed twice with water then dried (saturated NaCl, anhydrous MgSO4). The solution is filtered then concentrated to yield an oil (5.6 g) which is dissolved in ether then converted to the dioxalate salt by the addition of an ethereal solution of oxalic acid to yield 7.0 g, (72%) which decomposes at 152°–157° C. This material is twice recrystallized from ethyl acetate/methanol (10:1) to yield 2-(2-N,N-diethylaminoethyl)-4-(p-trifluoromethylphenoxy)-1,2,3,4-tetrahydroisoquinoline dioxalate (5.4 g, d@159°–160° C.

ANALYSIS: Calculated for $C_{22}H_{27}F_3N_2O \cdot 2(CO_2H)_2$: 54.54%C; 5.46%H; 4.89%N. Found: 54.78%; 5.43%H; 5.01%N.

EXAMPLE 29

2-(3-Piperidinopropyl)-1,2,3,4-tetrahydro-4-(p-trifluoromethylphenoxy)isoquinoline dioxalate To 100 ml n-butanol, is added 1,2,3,4-tetrahydro-4-(p-trifluoromethylphenoxy)isoquinoline of Example 8 (5.0 g, 0.017 mole), 3-piperidinopropyl chloride (5.1 g, 0.03 mole), $K_2CO_3$ (10 g), and 0.01 g. of KI.

After refluxing at 120° C. for three hours, the mixture is cooled, filtered and then n-butanol evaporated to yield an oil. The oil is stirred with 300 ml water for ten minutes, then extracted thrice with ether (100 ml). The ether extract is washed with water (100 ml), then dried (saturated NaCl, anhydrous MgSO4).

After filtering, the ether is evaporated to an oil, which is converted to a dioxalate salt by the addition of an ethereal solution of oxalic acid to yield 5.4 g (55%), m.p. 80° C. dec. This material is recrystallized twice from ethyl acetate to yield 2-(3-piperidinopropyl)-1,2,3,4-tetrahydro-4-(p-trifluoromethylphenoxy)isoquinoline dioxalate.

ANALYSIS: Calculated for $C_{24}H_{29}F_3N_2O \cdot 2(CO_2H)_2$: 56.18%; 5.56%H; 4.68%N. Found: 56.71%C; 5.55%H; 4.81%N.

EXAMPLE 30

4-(p-Chlorophenoxy)-6,7-dimethoxy-2-methyl-1,2,3,4-tetrahydroisoquinoline

To a suspension of NaH (50% in oil, treated with hexanes, 7.2 g, 0.15 mole), in 50 ml dry DMF is added a solution of 6,7-dimethoxy-2-methyl-1,2,3,4-tetrahydro-4-isoquinolinol (25.2 g, 0.113 mole) in 75 ml dry DMF. (The mixture becomes warm with evolution of gas.)

After stirring the mixture at 60° C. for one hour, it is cooled, then a solution of 4-chlorofluorobenzene (15.7 g, 0.12 mole) in 50 ml DMF is added, and the resultant mixture is stirred at 100° C. for seven hours.

The mixture is cooled, evaporated to an oil, stirred with 400 ml water for fifteen minutes, then extracted with chloroform. The chloroform layer is washed twice with water, then dried (saturated NaCl, anhydrous MgSO$_4$).

After filtering, the solvent is evaporated to an oil, which solidifies to a solid upon trituration with petroleum ether, 30.1 g, (80%), m.p. 107°–9° C. A sample of this material is recrystallized twice from ether/petroleum ether (1:5) to yield 4-(p-chlorophenoxy)-6,7-dimethoxy-2-methyl-1,2,3,4-tetrahydroisoquinoline, m.p. 112°–15° C.

ANALYSIS: Calculated for $C_{18}H_{20}ClNO_3$: 64.76%C; 6.04%H; 4.20%N. Found: 64.81%C; 6.14%H; 4.10%N.

EXAMPLE 31

4-(p-Nitrophenoxy)-1,2,3,4-tetrahydroisoquinoline maleate

4-Hydroxy-1,2,3,4-tetrahydroisoquinoline hydrochloride (6.7 g, 0.036 mole) is slowly added to a stirred suspension of sodium hydride (3.9 g, 0.079 mole), previously washed with hexanes, in dry DMF (65 ml). The reaction mixture is maintained at 0°–5° C. during the addition and then is slowly warmed to room temperature. After one hour the mixture is again cooled and a solution of 1-fluoro-4-nitrobenzene (5.6 g, 0.040 mole) in DMF (10 ml) is slowly added. The reaction mixture is stirred at room temperature for about 16 hours then is poured over ice water and extracted with dichloromethane. The combined organic extracts are washed with water then dried (saturated NaCl, anhydrous MgSO$_4$). The solution is filtered then concentrated to a semi-solid which is dissolved in methanol/ether, then converted to the maleate salt by the addition of an ethereal solution of maleic acid to yield 8.5 g, (61%) d@164° C. This material is twice recrystallized from ethyl acetate/methanol (5:1) to yield 4-(p-nitrophenoxy)-1,2,3,4-tetrahydroisoquinoline maleate, d 165°–166° C.

ANALYSIS: Calculated for $C_{15}H_{14}N_2O_3 \cdot C_4H_4O_4$: 59.06%C; 4.70%H; 7.25%N. Found: 58.84%C; 4.71%H; 7.17%N.

EXAMPLE 32

2-(3-N,N-Dimethylaminopropyl)-4-(p-nitrophenoxy)-1,2,3,4-tetrahydroisoquinoline dihydrochloride A mixture of 4-(p-nitrophenoxy)-1,2,3,4-tetrahydroisoquinoline of Example 31 (5.0 g, 0.018 mole), 3-dimethylaminopropyl chloride (4.5 g, 0.037 mole) and potassium carbonate (8.0 g) in n-butanol (100 ml) is refluxed for three hours. The mixture is cooled, filtered, then concentrated to an oil which is stirred with water then extracted with dichloromethane. The combined organic extracts are washed twice with water then dried (saturated NaCl, anhydrous MgSO$_4$). The solution is filtered and then concentrated to an oil (5.5 g) which is dissolved in methanol/ether and then converted to the dihydrochloride salt by the addition of ethereal hydrogen chloride. This material is immediately recrystallized from ethyl acetate/methanol (5:1) to yield 2-(3-N,N-dimethylaminopropyl)-4-(p-nitrophenoxy)-1,2,3,4-tetrahydroisoquinoline dihydrochloride (2.3 g, m.p. 188°–189° C.).

ANALYSIS: Calculated for $C_{20}H_{25}N_3O_3 \cdot 2HCl$: 56.08%C; 6.35%H; 9.81%N. Found: 56.22%C; 6.70%H; 9.76%N.

What we claim is:

1. A 4-aryloxy-1,2,3,4-tetrahydroisoquinoline having the formula

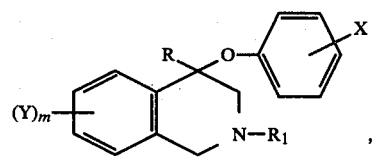

where Y is hydrogen and alkoxy of 1 to 6 carbon atoms; X is hydrogen, cyano, benzoyl, trifluoromethyl, phenyl, halogen, alkyl of 1 to 6 carbon atoms, alkoxy of 1 to 6 carbon atoms and nitro; R is hydrogen and alkyl of 1 to 6 carbon atoms; $R_1$ is hydrogen, alkyl and

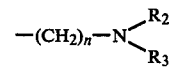

where $R_2$ and $R_3$ are the same or different and are hydrogen and alkyl of 1 to 6 carbon atoms or $R_2$ and $R_3$ are fused together to form a pyrrolidino or a piperidino ring substituent; m is an integer of 1 or 2; n is an integer of 2 or 3; and a pharmaceutically acceptable acid addition salt thereof.

2. The compound as defined in claim 1 which is 4-(o-cyanophenoxy)-2-methyl-1,2,3,4-tetrahydroisoquinoline or the pharmaceutically acceptable salt thereof.

3. The compound as defined in claim 1 which is 4-(p-cyanophenoxy)-2-methyl-1,2,3,4-tetrahydroisoquinoline or the pharmaceutically acceptable salt thereof.

4. The compound as defined in claim 1 which is 4-(p-benzoylphenoxy)-2-methyl-1,2,3,4-tetrahydroisoquinoline or the pharmaceutically acceptable salt thereof.

5. The compound as defined in claim 1 which is 2-methyl-1,2,3,4-tetrahydro-4-(p-trifluoromethylphenoxy)isoquinoline or the pharmaceutically acceptable salt thereof.

6. The compound as defined in claim 1 which is 2-methyl-4-(p-phenylphenoxy)-1,2,3,4-tetrahydroisoquinoline or the pharmaceutically acceptable salt thereof.

7. The compound as defined in claim 1 which is 4-(p-chlorophenoxy)-2-methyl-1,2,3,4-tetrahydroisoquinoline or the pharmaceutically acceptable salt thereof.

8. The compound as defined in claim 1 which is 2-methyl-4-phenoxy-1,2,3,4-tetrahydroisoquinoline or the pharmaceutically acceptable salt thereof.

9. The compound as defined in claim 1 which is 6,7-dimethoxy-2-methyl-1,2,3,4-tetrahydro-4-(p-trifluoromethylphenoxy)isoquinoline or the pharmaceutically acceptable salt thereof.

10. The compound as defined in claim 1 which is 4-(o-cyanophenoxy)-6,7-dimethoxy-2-methyl-1,2,3,4-tetrahydroisoquinoline or the pharmaceutically acceptable salt thereof.

11. The compound as defined in claim 1 which is 2-methyl-1,2,3,4-tetrahydro-4-(m-trifluoromethylphenoxy)isoquinoline or the pharmaceutically acceptable salt thereof.

12. The compound as defined in claim 1 which is 1,2,3,4-tetrahydro-4-(p-trifluoromethylphenoxy)isoquinoline or the pharmaceutically acceptable salt thereof.

13. The compound as defined in claim 1 which is 2-(3-dimethylaminopropyl)-1,2,3,4-tetrahydro-4-(p-trifluoromethylphenoxy)isoquinoline or the pharmaceutically acceptable salt thereof.

14. The compound as defined in claim 1 which is 4-(p-chlorophenoxy)-1,2,3,4-tetrahydroisoquinoline or the pharmaceutically acceptable salt thereof.

15. The compound as defined in claim 1 which is 1,2,3,4-tetrahydro-4-(m-trifluoromethylphenoxy)isoquinoline or the pharmaceutically acceptable salt thereof.

16. The compound as defined in claim 1 which is 2-(3-dimethylaminopropyl)-1,2,3,4-tetrahydro-4-(m-trifluoromethylphenoxy)isoquinoline or the pharmaceutically acceptable salt thereof.

17. The compound as defined in claim 1 which is 4-(p-chlorophenoxy)-2-(3-dimethylaminopropyl)-1,2,3,4-tetrahydroisoquinoline or the pharmaceutically acceptable salt thereof.

18. The compound as defined in claim 1 which is 2,4-dimethyl-1,2,3,4-tetrahydro-4-(p-trifluoromethyl phenoxy)isoquinoline or the pharmaceutically acceptable salt thereof.

19. The compound as defined in claim 1 which is 4-(o-methoxyphenoxy)-2-methyl-1,2,3,4-tetrahydroisoquinoline or the pharmaceutically acceptable salt thereof.

20. The compound as defined in claim 1 which is 2-methyl-4-(p-nitrophenoxy)-1,2,3,4-tetrahydroisoquinoline or the pharmaceutically acceptable salt thereof.

21. The compound as defined in claim 1 which is 2,4-dimethyl-4-(p-nitrophenoxy)-1,2,3,4-tetrahydroisoquinoline or the pharmaceutically acceptable salt thereof.

22. The compound as defined in claim 1 which is 2-phenoxycarbonyl-1,2,3,4-tetrahydro-4-(p-trifluoromethylphenoxy)isoquinoline or the pharmaceutically acceptable salt thereof.

23. The compound as defined in claim 1 which is 2-(2-N,N-dimethylaminoethyl)-1,2,3,4-tetrahydro-4-(p-trifluoromethylphenoxy)isoquinoline or the pharmaceutically acceptable salt thereof.

24. The compound as defined in claim 1 which is 2-(2-N,N-diethylaminoethyl)-1,2,3,4-tetrahydro-4-(p-trifluoromethylphenoxy)isoquinoline or the pharmaceutically acceptable salt thereof.

25. The compound as defined in claim 1 which is 2-(3-piperidinopropyl)-1,2,3,4-tetrahydro-4-(p-trifluoromethylphenoxy)isoquinoline or the pharmaceutically acceptable salt thereof.

26. The compound as defined in claim 1 which is 4-(p-chlorophenoxy)-6,7-dimethoxy-2-methyl-1,2,3,4-tetrahydroisoquinoline or the pharmaceutically acceptable salt thereof.

27. The compound as defined in claim 1 which is 4-(p-nitrophenoxy)-1,2,3,4-tetrahydroisoquinoline or the pharmaceutically acceptable salt thereof.

28. The compound as defined in claim 1 which is 2-(3-N,N-dimethylaminopropyl-4-(p-nitrophenoxy)-1,2,3,4-tetrahydroisoquinoline or the pharmaceutically acceptable salt thereof.

29. An anticonvulsant composition which comprises an anticonvulsant effective amount of a compound having the formula

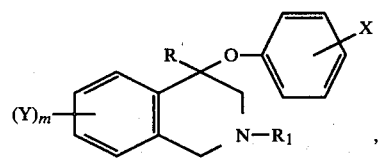

where Y is hydrogen and alkoxy of 1 to 6 carbon atoms; X is hydrogen, cyano, benzoyl, trifluoromethyl, phenyl, halogen, alkyl of 1 to 6 carbon atoms, alkoxy of 1 to 6 carbon atoms and nitro; R is hydrogen and alkyl of 1 to 6 carbon atoms; $R_1$ is hydrogen, alkyl and

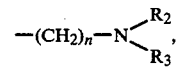

where $R_2$ and $R_3$ are the same or different and are hydrogen and alkyl or $R_2$ and $R_3$ are fused together to form a pyrrolidino or a piperidino ring substituent, m is an integer of 1 or 2; n is an integer of 2 or 3; and a pharmaceutically acceptable acid addition salt thereof.

30. An analgesic composition which comprises an effective analgesic amount of a compound having the formula

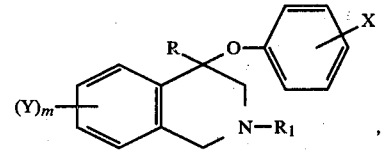

where Y is hydrogen and alkoxy of 1 to 6 carbon atoms; X is hydrogen, cyano, benzoyl, trifluoromethyl, phenyl, halogen, alkyl of 1 to 6 carbon atoms, alkoxy of 1 to 6 carbon atoms and nitro; R is hydrogen and alkyl of 1 to 6 carbon atoms; $R_1$ is hydrogen, alkyl of 1 to 6 carbon atoms and

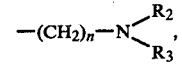

where $R_2$ and $R_3$ are the same or different and are hydrogen and alkyl of 1 to 6 carbon atoms or $R_2$ and $R_3$ are fused together to form a pyrrolidino or a piperidino ring substittuent; m is an integer of 1 or 2; n is an integer of 2 or 3; and a pharmaceutically acceptable acid addition salt thereof.

31. A diuretic composition which comprises a diuretically effective amount of a compound selected from the group consisting of 4-(p-cyanophenoxy)-B 2-methyl-1,2,3,4-tetrahydroisoquinoline, 2-(2-N,N-dimethylaminoethyl)1,2,3,4-tetrahydro-4-(p-trifluoromethylphenoxy)isoquinoline, 2-(2-N,N-diethylaminoethyl)-1,2,3,4-tetrahydro-4-(p-trifluoromethylphenoxy)isoquinoline, 2-(3-piperidinopropyl)-1,2,3,4-tetrahydro-4-(p-trifluoromethylphenoxy)isoquinoline and a pharmaceutically acceptable salt of any of the foregoing.

32. An antidepressant composition which comprises an antidepressant effective amount of a compound selected from the group consisting of 2-methyl-1,2,3,4-tetrahydro-4-(m-trifluoromethylphenoxy)isoquinoline, 2-methyl-4-(p-nitrophenoxy)-1,2,3,4-tetrahydroisoquinoline and a pharmaceutically acceptable acid addition salt of any of the foregoing.

* * * * *

UNITED STATES PATENT AND TRADEMARK OFFICE
CERTIFICATE OF CORRECTION

PATENT NO. : 4,375,471
DATED : March 1, 1983
INVENTOR(S) : Richard C. Effland, et al.

It is certified that error appears in the above—identified patent and that said Letters Patent is hereby corrected as shown below:

Column 1, lines 20-25: From "
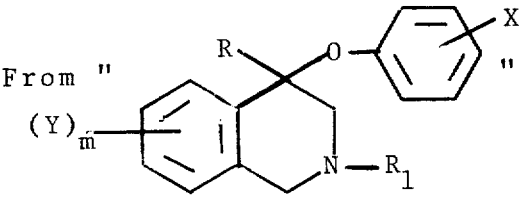
"

To: 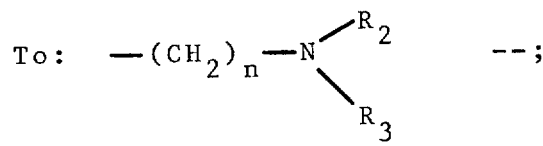 --;

Column 6, line 8: From "8 73" ;

To: --8 73 --;

Column 11, line 6: From "4(p-Tri..."

To: -- 4-(p-Tri... --.

Signed and Sealed this

Seventeenth Day of January 1984

[SEAL]

Attest:

GERALD J. MOSSINGHOFF

Attesting Officer    Commissioner of Patents and Trademarks